United States Patent [19]
Masse

[11] Patent Number: 5,377,413
[45] Date of Patent: * Jan. 3, 1995

[54] RETRACTING CUTTER

[76] Inventor: Joseph H. Masse, P.O. Box 63037, New Bedford, Mass. 02736-0898

[ * ] Notice: The portion of the term of this patent subsequent to May 11, 2010 has been disclaimed.

[21] Appl. No.: 60,347

[22] Filed: May 11, 1993

Related U.S. Application Data

[63] Continuation-in-part of Ser. No. 746,997, Aug. 19, 1991, Pat. No. 5,208,983.

[51] Int. Cl.⁶ .............................................. B25G 1/00
[52] U.S. Cl. .................................. 30/340; 30/169; 30/162; 7/900
[58] Field of Search ...................... 30/169, 164.5, 340, 30/368, 162; 7/900

[56] References Cited

U.S. PATENT DOCUMENTS

| | | | |
|---|---|---|---|
| 1,371,939 | 3/1921 | Simko | 30/169 |
| 2,589,501 | 3/1952 | Lenarduzzi | 30/164.5 |
| 4,452,106 | 6/1984 | Tartaglia | 7/900 |
| 4,484,368 | 11/1984 | Thompson | 7/900 |
| 4,890,351 | 1/1990 | Wilson | 30/169 |
| 5,208,983 | 5/1993 | Masse | 30/340 |

*Primary Examiner*—Richard K. Seidel
*Attorney, Agent, or Firm*—Ellen C. Childress

[57] ABSTRACT

A knife is disclosed having a self-retracting, adjustable blade. The handle of the knife has two pieces which when compressed expose the blade for use.

17 Claims, 12 Drawing Sheets

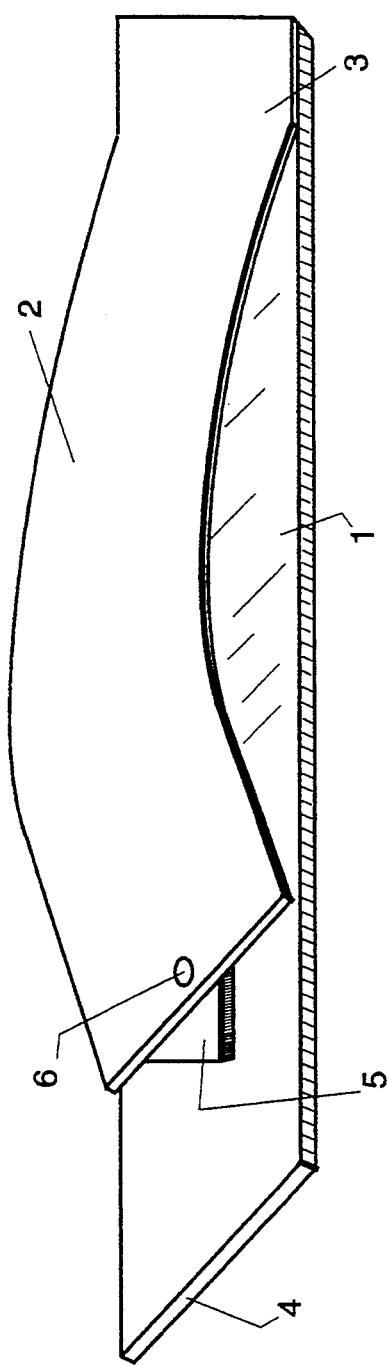
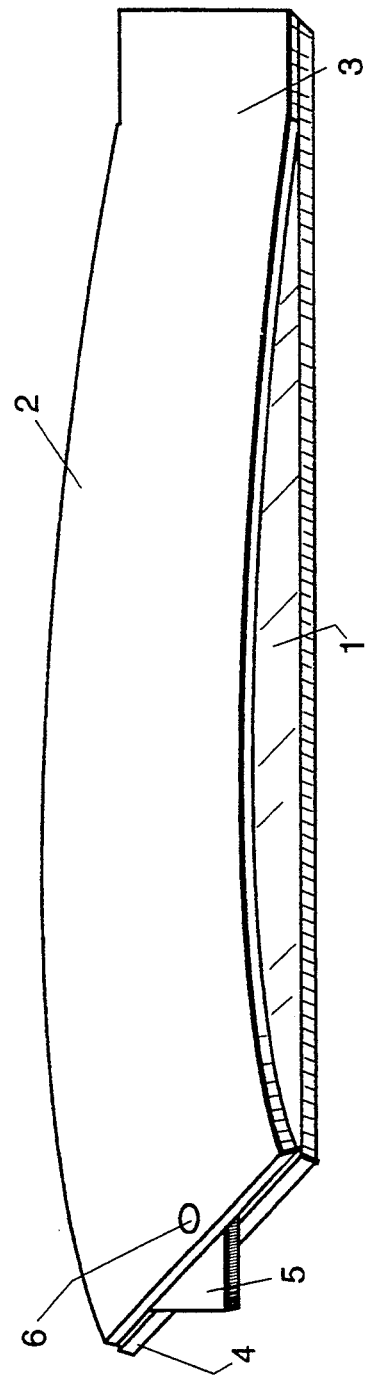

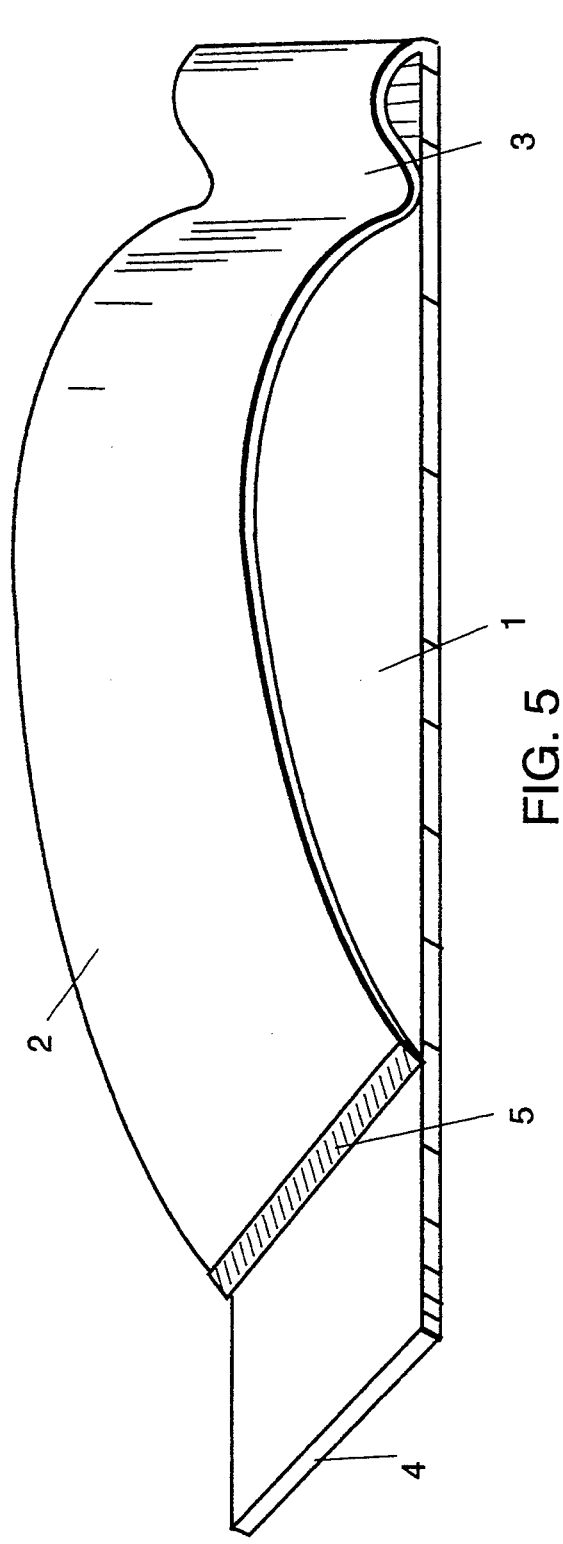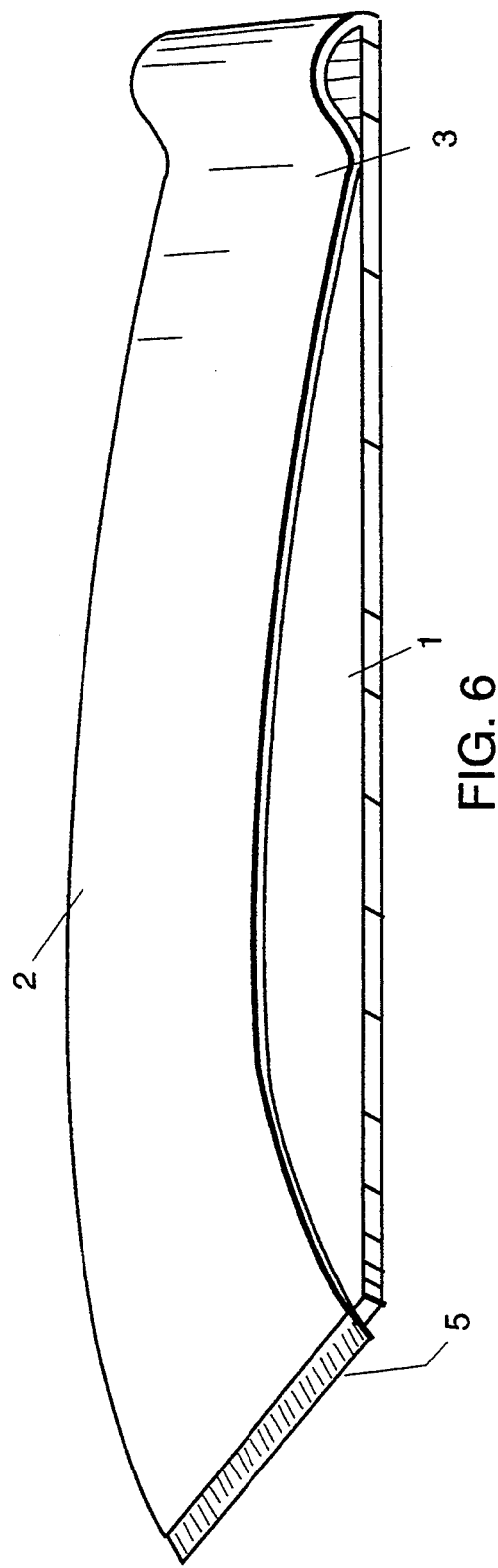

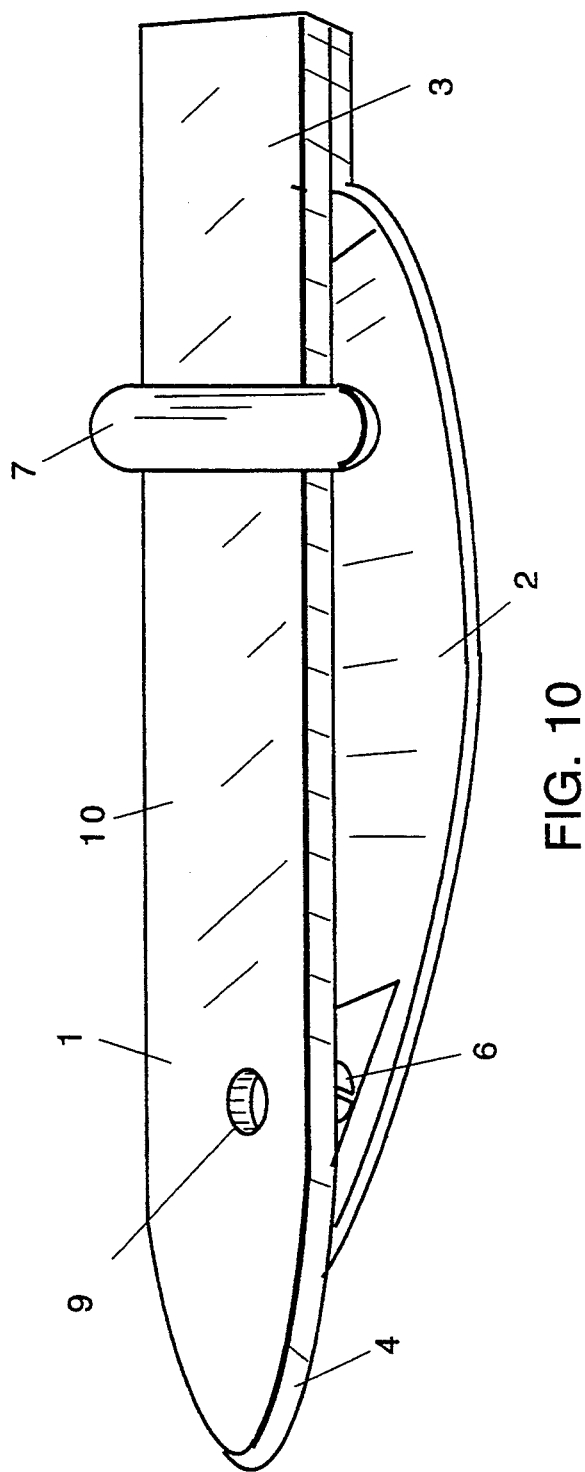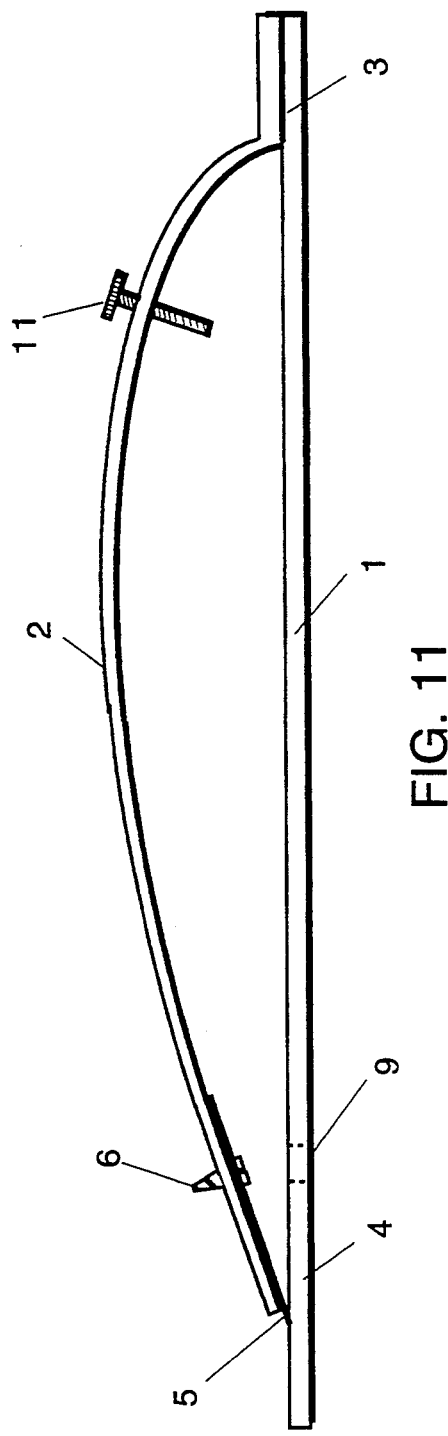

RETRACTING CUTTER

This application is a continuation-in-part of U.S. patent application Ser. No. 07/746,997 filed Aug. 19, 1991, now U.S. Pat. No. 5,208,983.

FIELD OF THE INVENTION

This invention relates to cutting tools and more particularly to hand held tools with retractable blades.

BACKGROUND OF THE INVENTION

Knives date from the Stone Age and are important to the present day. Exposed blades on knives can be a hazard and thus sheaths were developed to cover the blade. As early as the Roman Empire folding knives were developed. Such folding knives are called pocket or army knives and provide a safe means of carrying and storing bladed tools.

U.S. Pat. No. 2,037,914 discloses a knife offering razor sharpness. Such knives are now known as utility, shop or trimming knives. A variety of these knives have been developed including ones with retractable blades such as U.S. Pat. No. 4,733,734, which employs a button for retracting the blade. Crosses between pocket and utility knives are known.

A scalpel is a small lightweight knife used to cut tissue during dissection or surgery. For such use it is essential to control the depth of the cut since the number of layers or thickness of tissue to be cut varies. For a surgery, it is desirable to have a blade that automatically retracts to protect health care personnel against serum transmitted diseases such as AIDS and hepatitis B. Most scalpels use a disposable blade and holder. One such holder is described in U.S. Pat. No. 4,930,220, incorporated herein by reference.

Coupon cutters, designed to cut sections from newspapers and magazines also require control of the blade depth to avoid cutting extra pages. Additionally, it is desirable that such cutters be small enough to be carried about in a pocket or purse. Hook coupon cutters place a guide between the blade and the layer that is not to be cut. Others have a very small exposure of a nonadjustable blade.

Presently, sheathed blades require a specific movement by the user such as folding, unfolding or sliding a button. Operation takes conscious effort on the part of the user and sheathing mechanisms add substantially to the cost of manufacture.

However, the inventor is unaware of a self-retracting, adjustable depth knives of reasonable cost.

DESCRIPTION OF THE INVENTION

The subject invention of the application is a self-retracting, adjustable knife which operates by displacement due to compression. The handle of the knife is comprised of two legs of unequal length. The legs are attached to each other at one end and a blade is located at the unattached end of the longer arm. At least one of the legs is made from a resilient material. The longer leg is curved so that the blade's cutting edge rests against the shorter leg. The shorter leg is less curved, preferably straight. To use the knife the legs of the handle are compressed between the digits of the user, causing a displacement of the legs. If the longer leg is resilient, compression toward the shorter leg lengthens the effective length of the longer leg. The effective length refers to the length of a chord from the point of attachment to the unattached end of the shorter leg or the blade edge of the longer leg. If the shorter leg is resilient, compression into the curve of the longer leg shortens the effective length of the shorter leg. At rest, that is, not compressed, the effective length of the long leg is less than the effective length of the short leg, and the blade is retracted and unexposed. Under compression, the effective length of the long leg exceeds the effective length of the short leg, and the blade is exposed for use. The amount of blade exposed can be adjusted by controlling the amount of compression. When the compression is released, the knife automatically resumes its original safe position.

DESCRIPTION OF THE DRAWINGS

FIG. 1 is a perspective view of a retracted utility knife in accordance with the invention.

FIG. 2 is a perspective view of the knife shown in FIG. 1 in a displaced or exposed position.

FIG. 5 is a perspective view of a retracted utility knife having an integral blade in accordance with the invention.

FIG. 6 is a perspective view of the knife shown in FIG. 5 in a displaced or exposed position.

FIG. 10 is a back perspective view of the scalpel shown in FIG. 7.

FIG. 11 is side view of a scalpel having a screw to control the depth of the cut.

DESCRIPTION OF THE PREFERRED EMBODIMENTS

Figure 13:
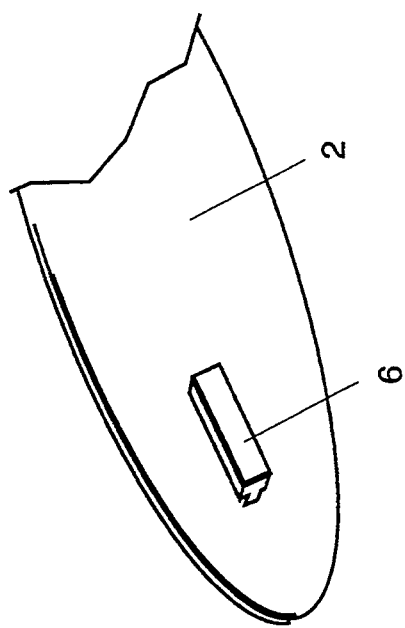
FIG. 13 is a detail of a tab for attachment for a scalpel blade.

FIGS. 1 through 4 show a self-retracting cutting tool having a rigid, straight leg 1 and a longer, resilient bent or bowed leg 2 attached at one end 3. Both legs are angled at the unattached end 4 to facilitate holding the tool at an angle. A blade 5 is located at the unattached end of the longer leg 2. Although the blade and leg may be integral, it is preferable some means of attachment 6 be used. The length of the longer leg 2 must be such that when fully bowed or bent, that is, in a resting state, no line from a point on attached end of the longer, resilient leg 2 to a point on the blade 5 is greater than a corresponding line from the same point of attachment to a corresponding point on the unattached end of the short leg 1 thus shielding the blade. In other words, the effective length of the longer leg is less than the effective length of the shorter leg at rest. Also, in this position the cutting edge of blade 5 is pressed against the shorter, rigid leg 1, so the blade does not catch on an unintended object. Suitable materials for resilient legs are spring metals such as steel, brass, and aluminium, or a resilient plastic such as polyethylene or polypropylene. Suitable materials for the rigid legs are steel, brass, aluminium, plastic or ceramic. Both legs may be made of the same material, however, it is preferable that the thickness of shorter leg 1 be greater than the thickness of the longer leg 2 for added resiliency of the longer leg 2. Commercially available blades, such as breakaway blades available from Stanley tools may be attached by a cement such as super-glue, solder, spotwelding, by a screw, molded in, by a tab such as shown in FIG. 13, by the tension holder disclosed in FIGS. 14, 15 and 16, or any convenient method which does not obstruct the use of the knife. Since most blades are flat, the section of the longer, resilient leg 2 resting against the blade 5 is flat. In use the legs are compressed between the user's digits, displacing the longer leg 2. When compressed the effective length of the longer, resilient leg 2 (that is from the attachment point along the curve to the cutting edge of the blade) must be greater than the effective length of the shorter, rigid leg 1. As the longer leg 2 is displaced, the blade 5 is exposed for use. If light pressure is used, the blade 5 is displaced only slightly, allowing for a shallow cut, heavier pressure exposes more of the blade for a deeper cut. The depth of the cut is adjusted by varying the amount of compression. When compression is released, the blade 5 automatically retracts to its safe position.

FIGS. 5 and 6 show a knife made from one piece of material. In this embodiment the blade 5 has been formed from the unattached end of the longer leg 2. Tapering the material results in a more resilient leg with less thickness than the rigid leg. If steel is used, the blade edge can be heat treated to retain sharpness.

The relationship between the amount and placement of the bowing or bending of the curved leg 2 and the amount of blade 5 exposed can be estimated by inscribing a right triangle having a height from the point of pressure on the curved leg to the nearest point on the straight leg, having a base along the straight leg from the blade to the point formed by the intersection of the height with the base, and having a hypotenuse from the point of pressure to the blade. As the height is decreased, by pressure, and the hypotenuse remains constant, the base of the triangle increases. The change in height of the triangle defines the displacement at the pressure point, and the change in the base of the triangle defines the displacement of the blade. The ratio of blade displacement to displacement of the pressure point can be approximated by the ratio of the difference between the sines to the difference between the cosines of the angles formed by the first triangle leg and the hypotenuse at the initial and final positions. It has been found that knives having a blade to pressure point displacement ratio of 1:4 are satisfactory. The amount of bending or bowing may be adjusted to give a degree of control of depth suitable for the desired application. Metal can be bent for the knife on a bending machine such as described in U.S. Pat. No. 5,007,269 incorporated herein by reference. Alternatively the knife could be molded from a resilient plastic. By placing a blade in the plastic, the plastic could serve as a stop to further control the depth of the cut.

Figure 3:
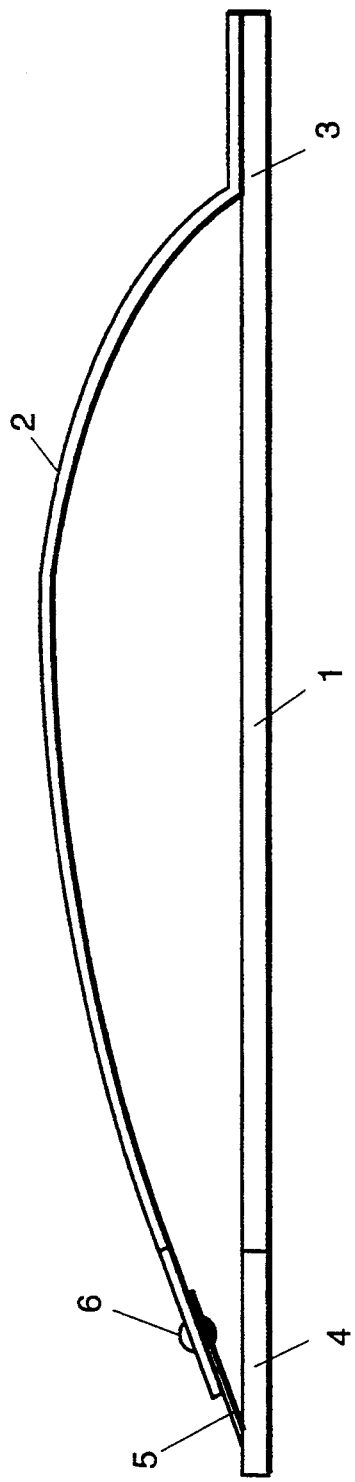
FIG. 3 is a side view of the knife shown in FIG. 1.
Figure 4:
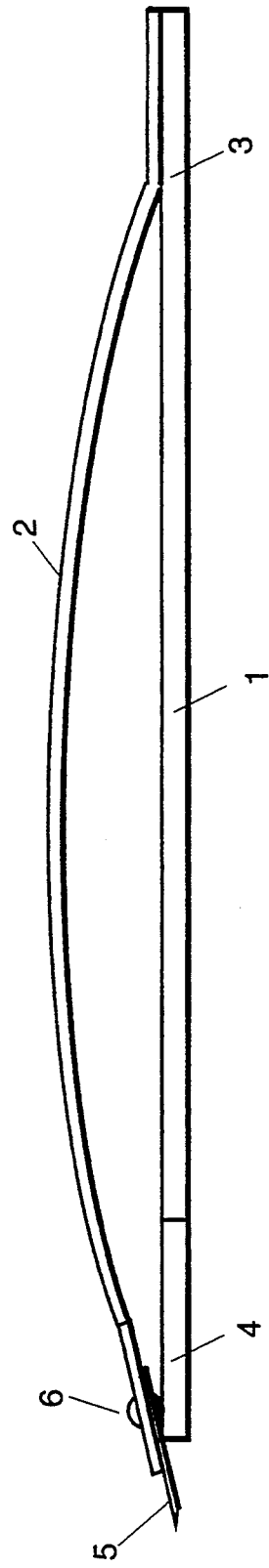
FIG. 4 is a side view of the knife as shown in FIG. 2
Figure 7:
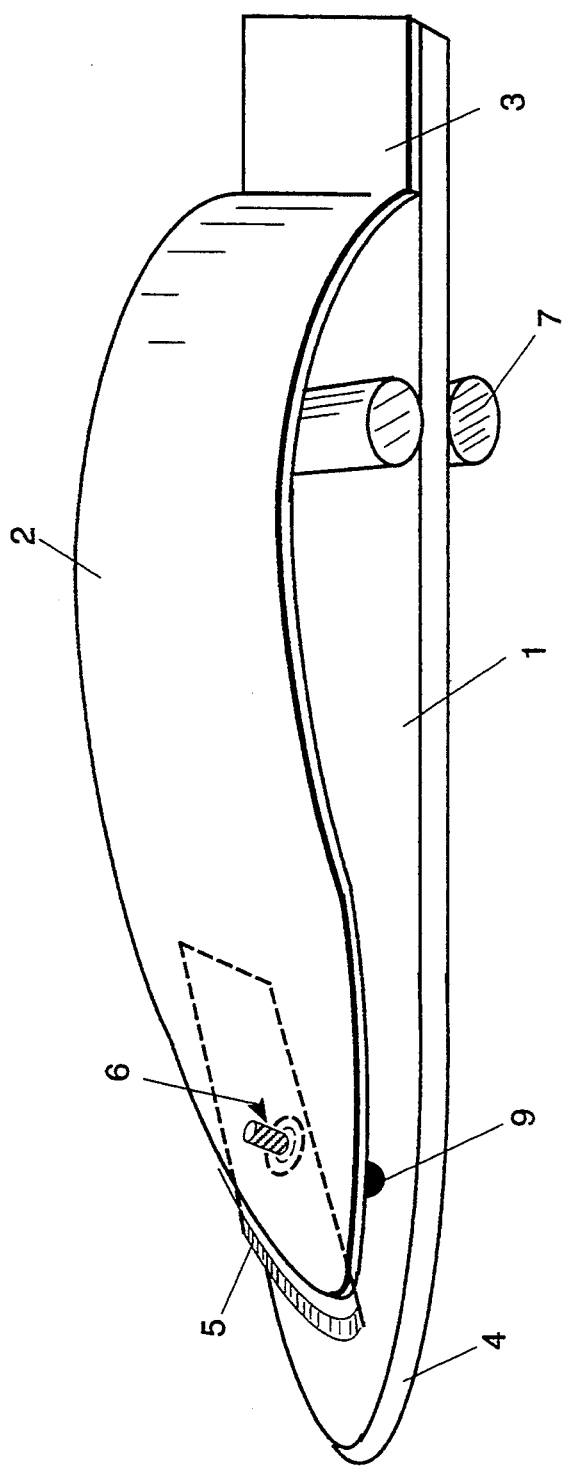
FIG. 7 is a front perspective view of a scalpel having a in the retracted position in accordance with the invention.
Figure 8:
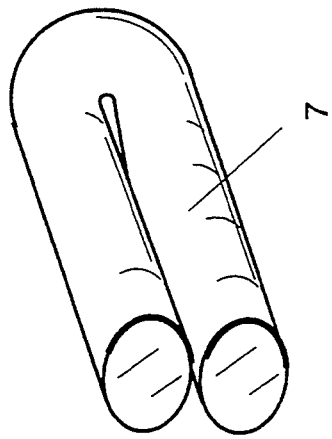
FIG. 8 is a perspective of the removable stop 7 shown in FIGS. 7 and 10.

The scalpel shown in FIGS. 7 and 10 has a stopping device for precise control of displacement and therefore the depth of a cut. The stopping device 7 is a clip which slides on the leg of the scalpel and can be preset to a particular displacement. The clip can be easily removed. Such displacement control devices can be used with other embodiments. The scalpel is designed to take advantage of commercially available blades such as those shown in FIG. 9. In this embodiment, the longer leg 2 is tapped for a screw 6 which fits through opening 8 in the blade. Access to the head of the screw 6 is made via an aperture 9 in the rigid leg 1. Any suitable means of attaching blades could be used such as tab, or holder such as described in U.S. Pat. No. 4,930,220. The preferred material for scalpels is stainless steel. The scalpel of FIG. 10 is provided with textured legs to provide a better grip.

The scalpel of FIG. 11 has a similar means of securing 6 the blade 5 to that in FIGS. 7 and 10, but the means of controlling the amount of displacement is a screw 11.

Figure 12:
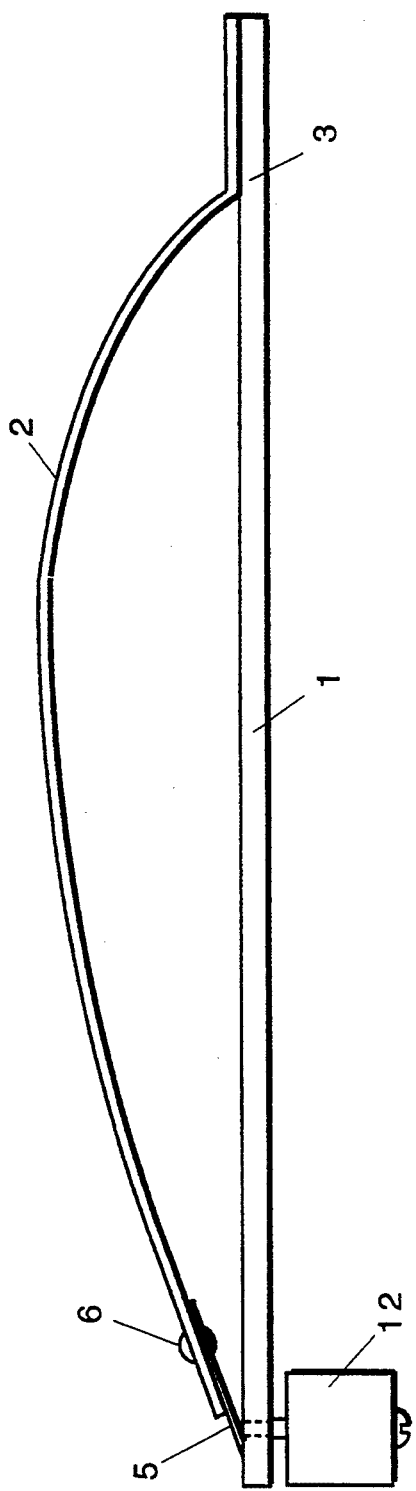
FIG. 12 is a side view of a knife with a roller.

The knife shown in FIG. 12 has a roller 12 attached to the shorter leg 1. This wheel reduces friction when the knife is used on soft material such as rubber or tissue.

Figure 9:
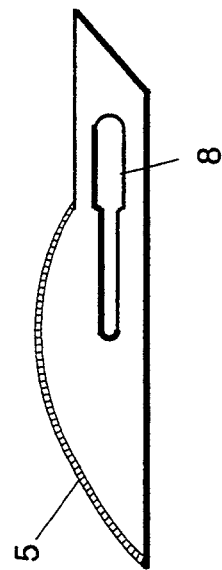
FIG. 9 is a front perspective view of a commercially available scalpel blade.

The detail in FIG. 13 shows a tab 6 fop attaching a commercially available scalpel blade 5 as shown in FIG. 9. The tab has a "T" shaped cross section. The cross bar of the T is slightly narrower than the width of the widest part of the slot 8 in the blade 5. The stem is substantially the same as the width of the narrow section of the slot 8 in the blade 5.

Figure 14:
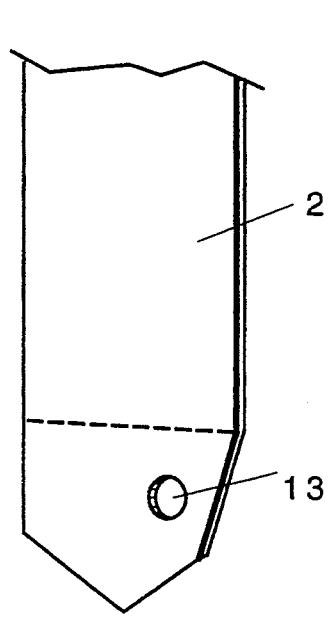
FIG. 14 is a perspective view of a detail of a tension holder for a blade before bending.
Figure 15:
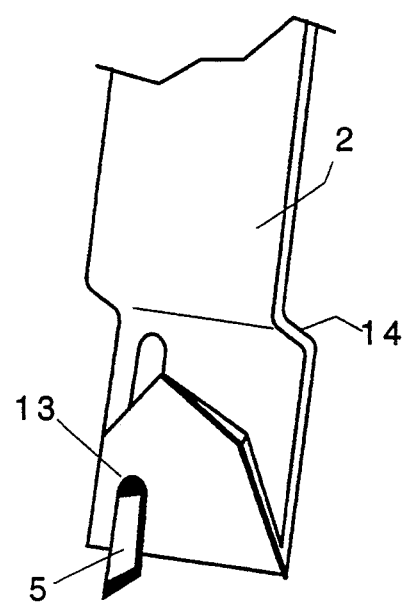
FIG. 15 is a perspective view of a detail of a knife showing the completed tension holder with disposable blade
Figure 16:
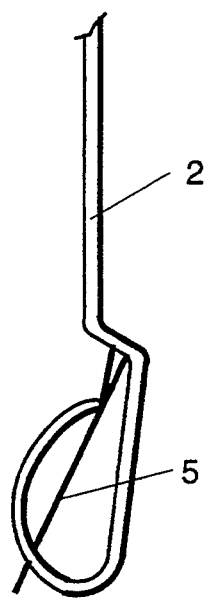
FIG. 16 is a side view of the detail shown in FIG. 15.

FIGS. 14 and 15 show a blade holder based on tension and method of making the same. An aperture 13 is drilled or stamped in the unattached end of the longer leg 2. The leg 2 is then bent to form a U having a ridge 14 at the upper end. The blade 5 is then installed by pressing against a wood or a soft metal to force it into the aperture. Upon being forced in the blade will bend slightly. The blade 5 can be removed with pliers.

Figure 17:
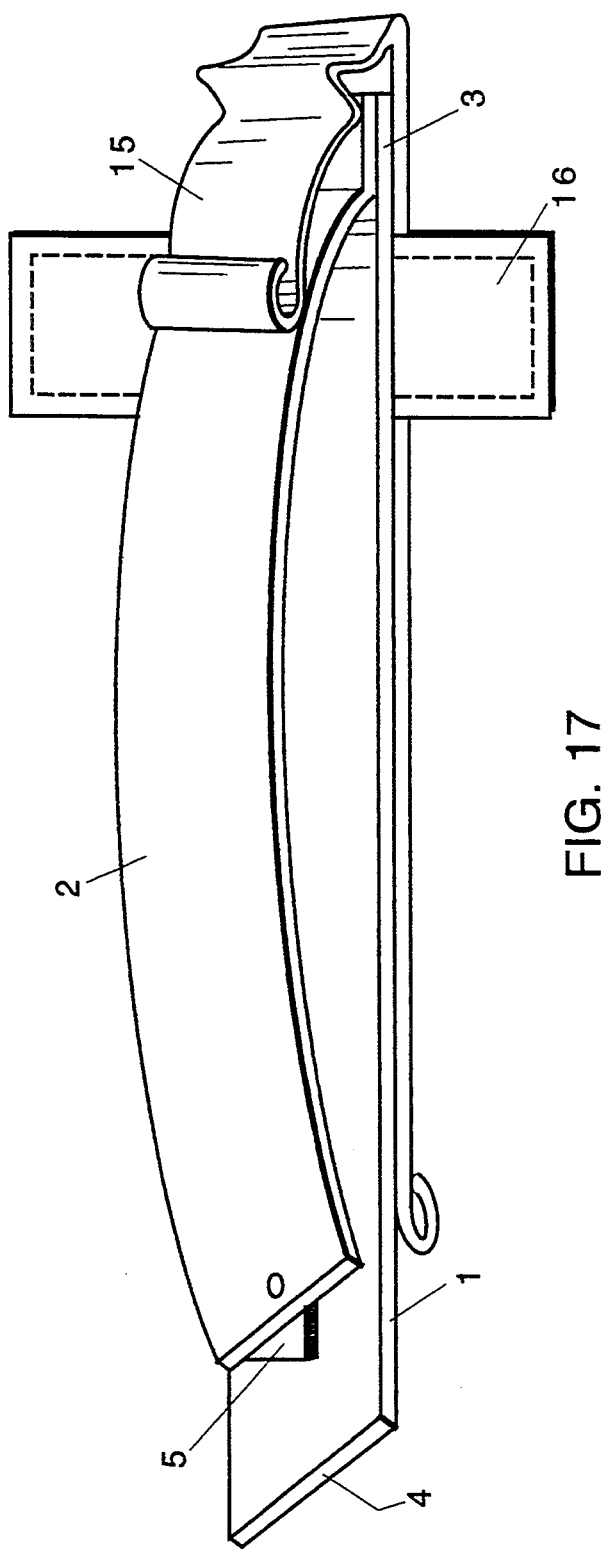
FIG. 17 is a perspective view of a combination knife-clip.
Figure 18:
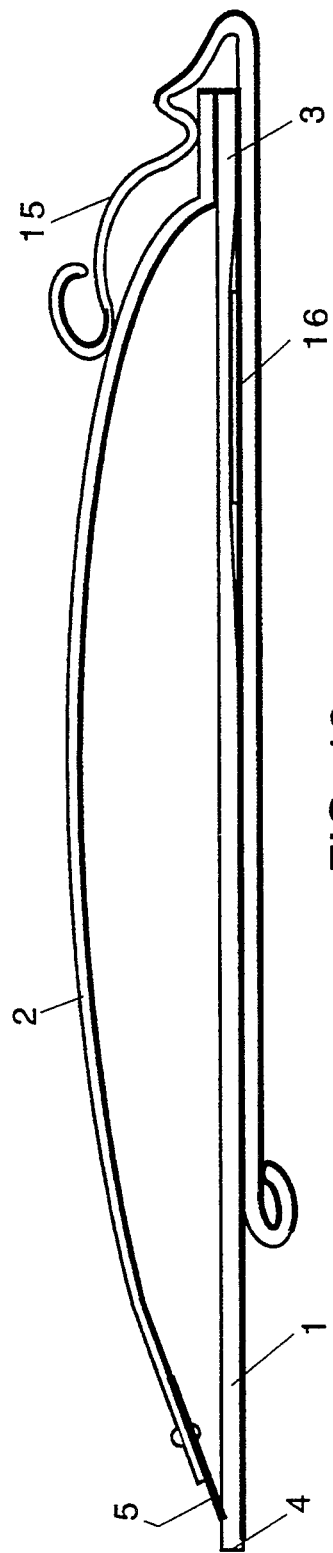
FIG. 18 is a side view of a combination knife-clip.

The knife can be modified to combine with other useful objects such as a paper clip, pocket clip, bookmark, money clip or tweezers. FIGS. 17 and 18 show one such modification for clipping to a lapel or the top of a shirt pocket 16 or as a business card holder. In the knife shown, the knife is clipped with a outer resilient handle 15, which may be removable. The handle also serves to stiffen the shorter leg 1.

Figure 20:
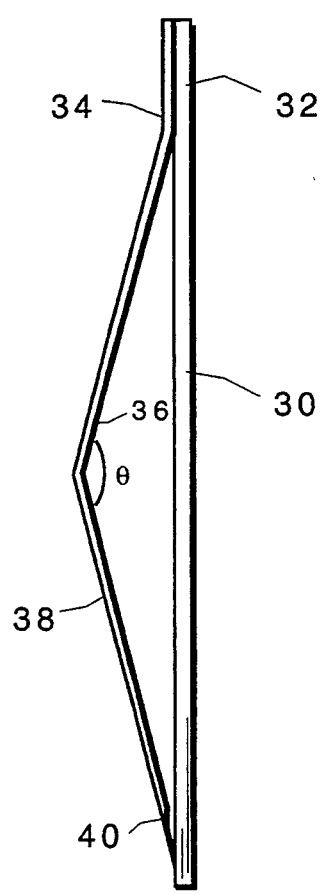
FIG. 20 is a side view of a knife having legs formed with straight segments.
Figure 22:
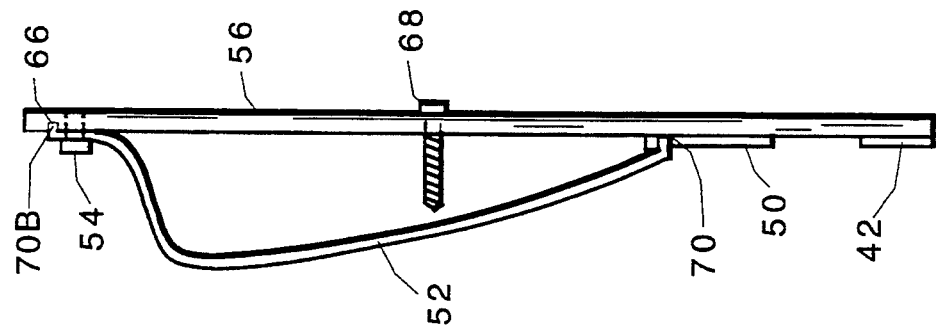
FIG. 22 is a side view of the cutter of FIG. 21.

The knives thus described have all shown legs which have a rounded curve. However, as shown in FIG. 20, straight segmented curves will also work. The shorter less curved leg 30 (in this case straight) is fastened at its upper end 32 to the longest leg upper end 34. The longer leg has two straight segments 36 and 38 forming an angle 0. Pressure on the longer leg extends the blade 40 for use. Of course the longer leg may employ several straight segments or combinations of straight and rounded curves.

Figure 24:
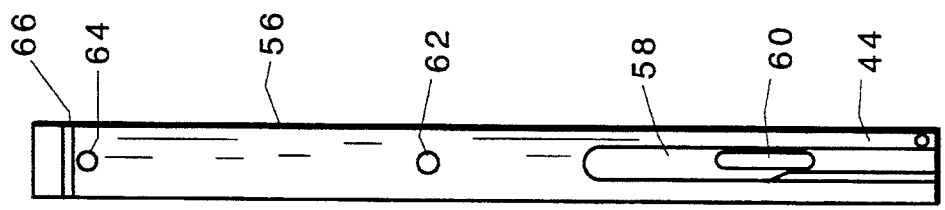
FIG. 24 is a top view of the cutter of FIG. 21 with the top removed.
Figure 21:
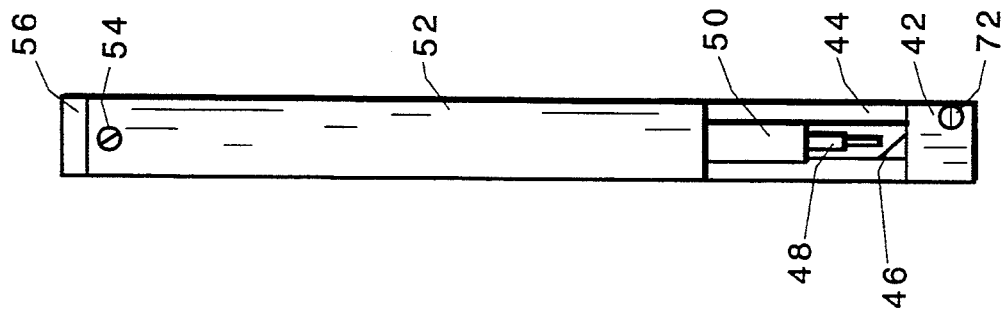
FIG. 21 is a top view of a retracting cutter having a sliding blade held by a key block.
Figure 23C:
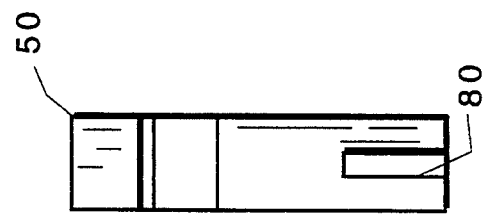
FIGS. 23 A, 23 B, and 23 C are top, side and bottom views of the key block for the cutter of FIG. 21.
Figure 23B:
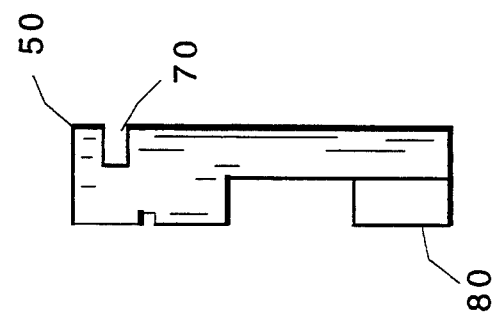
Figure 23A:
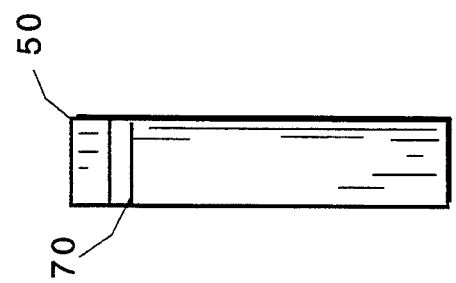

FIGS. 21 and 24 show an alternative scalpel, in which the longer leg is formed by a curved section 52, a key block 50 and a scalpel blade 46. The shorter less curved leg 56 has a slot 66 at the upper end, an aperture 62 for a depth control screw 68, and a groove 58 for retaining and guiding a scalpel blade 46. The groove 58 has a hole for easier access to the blade 46. The slot 66 in the upper end receives an upper lip 70B of the upper leg curved section 52 To further secure the section 52, a screw 54 passes through the leg into an aperture 64 in the shorter leg 56. The scalpel blade 46 lies loosely in the groove 58 between ridges 44. To secure the tip of the blade, a plate 42 covers the lower section of the groove and is held in place by screw 72. A longitudinal ridge 80 of the key block 50 is placed in the scalpel blade slot 48. A groove 70 on the opposing side of the key block 50, engages a second lip 70B of the upper leg curved section 52. This arrangement provides for easy blade replacement and accurate depth control.

Figure 19:
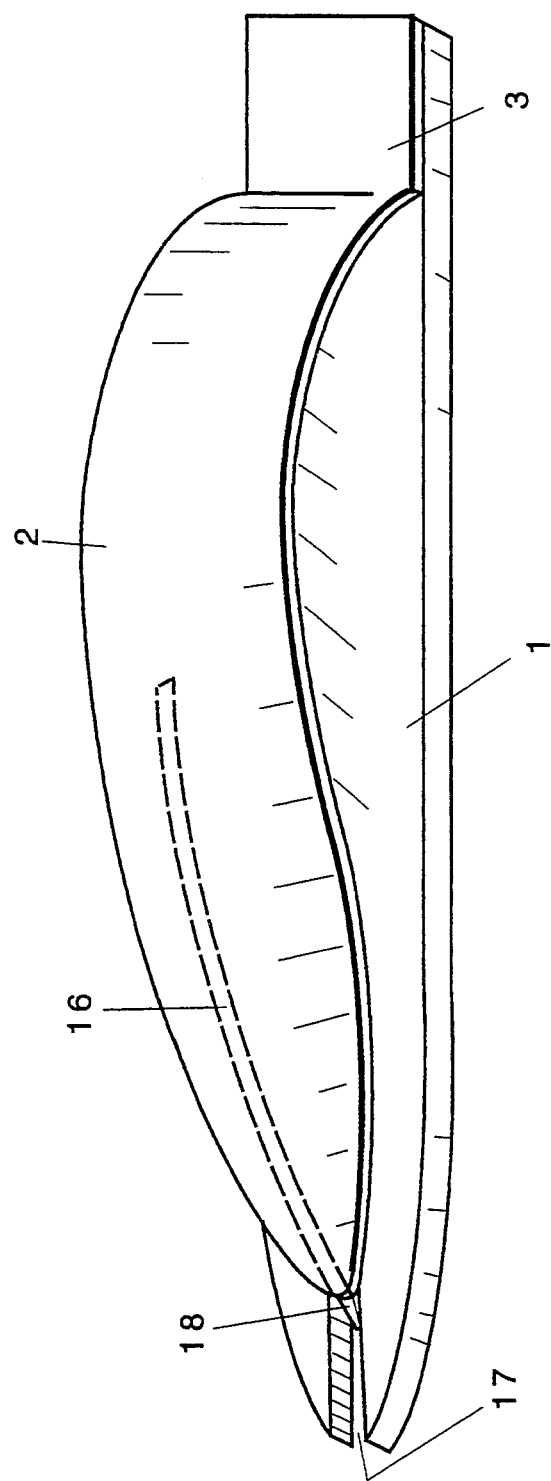
FIG. 19 is a perspective view of a pen.

Although the tool thus far described is a knife, the retracting handle could be modified for other tools such as a punch, writing implement, string cutter, micro probe or gauge. If the tip of the tool cannot slide over the surface of the shorter leg, the longer leg could be grooved or notched to allow for protection of the tool. FIG. 19 shows a pen with a flexible refill 16 attached to the longer leg 1 and a groove 17 to protect the pen point 18.

A string cutter could be formed by cutting a notch in the shorter leg to guide the string.

The tools disclosed in this invention are inexpensively manufactured, easy to use, and require no complicated adjustments. Automatic retraction ensures the tool is safely out of the way when not in use. These tools could be carried in the purse or pocket of the user, being handy for clipping items from newspapers, plastic unopened seals from containers, bubble wrap, leather, and layers of tissue.

What is claimed is:

1. An adjustable self-retracting instrument comprising:
   (a) a primary functional section of said instrument;
   (b) a first curved leg having upper and lower ends, said section being located at the lower end of said first leg; and
   (c) a second shorter less curved leg having upper and lower ends, wherein at least one leg is made from a resilient material, said second leg being attached to said first leg at the upper end and resting against said section, whereby when said legs are compressed together said section extends beyond said second leg.

2. The instrument of claim 1 wherein said section is chosen from the group consisting of points, blades and probes.

3. The instrument of claim 1 wherein said instrument is a knife and said section is a blade.

4. The instrument of claim 1 wherein said first curved leg has at least one straight section.

5. The instrument of claim 4 wherein said leg has two straight sections which form a nonstraight angle.

6. The instrument of claim 1 wherein said first leg further comprises:
   a blade;
   a key block; and
   a curved section.

7. The instrument of claim 6 wherein said blade further comprises:
   a scalpel blade having a slot, and said key block has a projection for engaging said slot.

8. The instrument of claim 7 wherein said key block has a groove and said curved section has at least one lip, said groove receiving said lip.

9. The instrument of claim 8 wherein said curved section has two lips and said second leg has an opening for receiving said lips.

10. The instrument of claim 6 wherein said second leg has a slot for resting said blade in.

11. The instrument of claim 10 wherein said second arm further comprises a plate for covering a portion of said blade slot.

12. The instrument of claim 6 wherein said curved section is detachable.

13. The instrument of claim 12 wherein said curved section has at least one lip and said second leg has an opening for receiving said lip.

14. The instrument of claim 6 further comprising:
   means for controlling the depth of a cut made by said blade.

15. The instrument of claim 14 wherein said means further comprises:
   a threaded controller located in said second leg.

16. The instrument of claim 6 wherein at least one leg is textured

17. The instrument of claim 6 wherein said lower ends of said legs are angled to facilitate holding said knife at an angle.

* * * * *